United States Patent
Agnihotri et al.

(10) Patent No.: US 10,318,709 B2
(45) Date of Patent: Jun. 11, 2019

(54) METHOD AND SYSTEM FOR CROSS-MODALITY CASE-BASED COMPUTER-AIDED DIAGNOSIS

(75) Inventors: Lalitha Agnihotri, Hartsdale, NY (US); Lilla Boroczky, Mount Kisco, NY (US); Luyin Zhao, Lawrenceville, NJ (US)

(73) Assignee: Koninklijke Philips N.V., Eindhoven (NL)

( * ) Notice: Subject to any disclaimer, the term of this patent is extended or adjusted under 35 U.S.C. 154(b) by 1076 days.

(21) Appl. No.: 12/747,602

(22) PCT Filed: Dec. 9, 2008
(Under 37 CFR 1.47)

(86) PCT No.: PCT/IB2008/055184
§ 371 (c)(1),
(2), (4) Date: Jun. 11, 2010

(87) PCT Pub. No.: WO2009/083837
PCT Pub. Date: Jul. 9, 2009

(65) Prior Publication Data
US 2010/0272338 A1    Oct. 28, 2010

Related U.S. Application Data

(60) Provisional application No. 61/015,919, filed on Dec. 21, 2007.

(51) Int. Cl.
*G06F 19/00* (2018.01)
*G16H 50/70* (2018.01)
*G16H 50/20* (2018.01)

(52) U.S. Cl.
CPC ........... *G06F 19/321* (2013.01); *G16H 50/70* (2018.01); *G16H 50/20* (2018.01)

(58) Field of Classification Search
CPC ........................... G06F 19/321; G06F 19/322
USPC .................... 705/2–3; 600/300; 382/128–134
See application file for complete search history.

(56) References Cited

U.S. PATENT DOCUMENTS

| 7,640,051 B2 | 12/2009 | Krishnan et al. |
| 7,899,225 B2 * | 3/2011 | Collins et al. ............... 382/128 |
| 8,108,024 B2 | 1/2012 | Carlsen et al. |
| 2003/0103663 A1 * | 6/2003 | Li et al. ....................... 382/131 |
| 2004/0020496 A1 | 2/2004 | Campbell et al. |

(Continued)

FOREIGN PATENT DOCUMENTS

| JP | 07-322081 | 8/1995 |
| JP | H1170083 A | 3/1999 |

(Continued)

OTHER PUBLICATIONS

Lehmann, T. M., et al.; Content-based Image Retrieval in Medical Applications; 2004; Methods inf Med; 43:354-361.

(Continued)

*Primary Examiner* — Linh Giang Le

(57) ABSTRACT

A system and method for cross-modality case-based computer-aided diagnosis comprises storing a plurality of cases, each case including at least one image of one of a plurality of modalities and non-image information, mapping a feature relationship between a feature from images of a first modality to a feature from images of a second modality, and storing the relationship.

14 Claims, 4 Drawing Sheets

| Scans / Patient ID | Film Mammogram | Ultrasound | MRI | Digital Mammogram |
|---|---|---|---|---|
| 1 | x | - | x | - |
| 2 | x | x | x | - |
| 3 | - | x |   | x |
| .. |   |   |   |   |
|   | x | - | x |   |
| N | x | - | - | x |

(56) References Cited

U.S. PATENT DOCUMENTS

| | | | |
|---|---|---|---|
| 2004/0204965 A1* | 10/2004 | Gueck et al. | 705/3 |
| 2007/0023737 A1 | 2/2007 | Mears | |
| 2008/0130970 A1* | 6/2008 | Niemeyer et al. | 382/128 |
| 2009/0138432 A1 | 5/2009 | Agnihotri et al. | |

FOREIGN PATENT DOCUMENTS

| | | |
|---|---|---|
| JP | H1173490 A | 3/1999 |
| JP | 2001346042 A | 12/2001 |
| JP | 2006-108805 | 4/2006 |
| JP | 2007275440 A | 10/2007 |
| JP | 2007279942 A | 10/2007 |
| JP | 2007286945 A | 11/2007 |
| JP | 2007307290 A | 11/2007 |

OTHER PUBLICATIONS

Maes, F., et al.; Multimodality Image Registration by Maximization of Mutual Information; 1997; IEEE Trans. on Medical Imaging; 16(2)187-189.

Malik, A., et al.; Classification of Medical Images Using Energy Information Obtained from Wavelet Transform for Medical Image Retrieval; 2005; Proc. of Enterprise Networking and computing in Healthcare Industry; pp. 124-129.

Rahman, M. M., et al.; Medical Image Retrieval and Registration: Towards Computer Assisted Diagnostic Approach; 2004; Proc. of Ideas Workshop on Medical Information Systems: The Digital Hospital; pp. 78-89.

Sarkar, A., et al.; Comparison of Manual vs. Automated Multimodality (CT-MRI) Image Registration for Brain Tumors; 2005; Medical Dosimetry; 30(1)20-24.

Van Den Elsen, P. A., et al.; Grey value correlation techniques used for automatic matching of CT and MR brain and spine images; 1994; Proc. of the SPIE; vol. 2359:227-237.

Koji Watanabe: 'Multi-modality image alignment and superposition' Japan Journal of Radiological Technology magazine vol. 59 No. 1, Jan. 2003 pp. 60-65.

* cited by examiner

| Scans / Patient ID | Film Mammogram | Ultrasound | MRI | Digital Mammogram |
|---|---|---|---|---|
| 1 | x | - | x | - |
| 2 | x | x | x | - |
| 3 | - | x | | x |
| .. | | | | |
| | x | - | x | |
| N | x | - | - | x |

| Feature / Modality | Spiculation | Density | Texture | Avg. gray value |
|---|---|---|---|---|
| CT | 1 | 1 | 1 | 1 |
| Ultrasound | 0.2 | 0.5 | 2 | 0.4 |
| MRI | 5 | 3 | 0.2 | 6 |
| X-Ray | 1.5 | 2 | 1 | 3 |
| PET | | | | |
| ... | | | | |

Y-axis = Feature A from Image Modality Y

X-axis = Feature A from Image Modality X

METHOD AND SYSTEM FOR CROSS-MODALITY CASE-BASED COMPUTER-AIDED DIAGNOSIS

FIELD OF INVENTION

The present application generally relates to systems and methods for a cross-modality case-based computer aided diagnosis ("CADx"). Specifically, the system and methods may allow for a user of a CADx system to retrieve similar cases across different imaging modalities.

BACKGROUND

A case-based CADx system is based on the idea that clinicians acquire knowledge by experience and referring to cases that they have seen before. One way, in which a decision support system can assist a clinician in making a diagnosis based on a CT scan (or any other modality scans X-rays, magnetic resonance imaging (MRI), ultrasound, positron emission tomography (PET), etc.) of for example, lung cancer, is to offer previous cases that have been diagnosed and are similar to the one in question. A case-based paradigm is that pulmonary nodules similar to the one to be diagnosed are retrieved from a database of nodules with known diagnosis and presented to the radiologist. This is the basic premise of a case-based CADx system.

Case-based CADx typically involves fetching, from a database, information particular to a disease, such as tumors or lesions with known pathology, i.e., malignant or benign. The information typically includes a diagnostic scan of tumors that have already been diagnosed for visual comparison with the diagnostic scan of the tumor to be diagnosed. The tumor may be in the patient's lung, for example. A diagnostic scan of the tumor may be captured by any one of a number of imaging techniques, some of which are mentioned above. From the scan, features of a tumor may then be calculated, each feature representing a particular visual characteristic of the tumor. The tumor to be diagnosed, and the tumors of the database, can be placed in a common feature space, i.e., an N-dimensional space for which each dimension represents a respective one of N measured features. Similarity between any tumor of the database and the tumor to be diagnosed can tentatively and objectively be assessed based on proximity of the two tumors in the feature space. Typically, from the database the tumors with closest proximity are fetched as similar tumors. The fetched examples may be displayed alongside the tumor to be diagnosed, for visual comparison. Case-based CADx can also be useful in training medical personnel in diagnosing different diseases.

SUMMARY OF THE INVENTION

The present invention is directed to a method comprising the steps of storing a plurality of cases, each case including at least one image of one of a plurality of modalities and non-image information, mapping a feature relationship between a feature from images of a first modality to a feature from images of a second modality, and storing the relationship. In another aspect, the method further comprising the steps of extracting a feature from an original image, retrieving at least one case based on the extracted feature and the feature relationship, and simultaneously displaying the original image and the retrieved case.

A system, comprising a memory storing a plurality of cases, each case including at least one image of one of a plurality of modalities and non-image information and a processor mapping a feature relationship between a feature from images of a first modality to a feature from images of a second modality and storing the feature relationship in the memory. In another aspect, the processor further extracts a feature from an original image, retrieves at least one of the stored cases based on the extracted feature and the feature relationship, and simultaneously displays the original image and the retrieved case.

A system, comprising a means for storing a plurality of cases, each case including at least one image of one of a plurality of modalities and non-image information and a means for mapping a feature relationship between a feature from images of a first modality to a feature from images of a second modality and storing the relationship in the memory.

DETAILED DESCRIPTION

Figures 1, 2, 3:
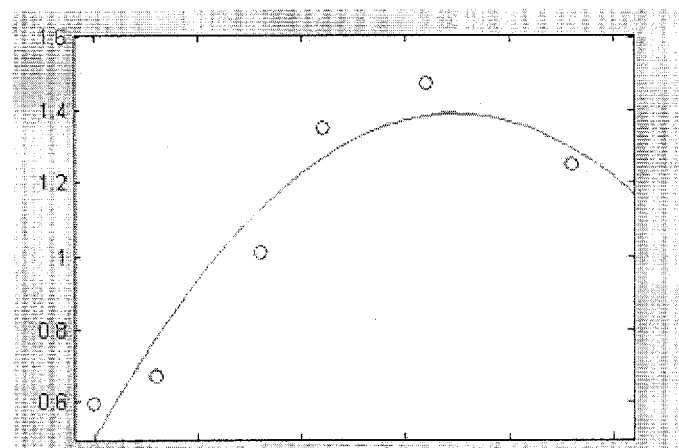
FIG. 1 shows an exemplary database for the cross-modality case-based CADx system consisting of patients with breast cancer and the imaging scans that the patients have had, according to the present invention.
FIG. 2 shows an exemplary CADx system database of relative feature ratios across imaging modalities, according to the present invention.
FIG. 3 shows an exemplary estimation of features in one image modality to another using a polynomial function.

The present invention may be further understood with reference to the following description of exemplary embodiments and the related appended drawings, wherein like elements are provided with the same reference numerals. The exemplary embodiments of the present invention are related to a system and methods for using a case-based computer aided diagnosis ("CADx") system to retrieve previously diagnosed cases including multimodality images (e.g., CT scans, MRI, ultrasound, etc.) and patient information, which are similar to a case in question based on a single modality image. Specifically, the exemplary system and method may allow for a user (e.g., a clinician, physician, radiologist, etc.) of the case-based CADx system to retrieve cases with multimodality images that are similar to the scan of original modality (scan being analyzed) of the patient in question based on the mapping of features in the original modality to features in other modalities. Retrieved cases may be simultaneously displayed with the case in question for comparison.

A cross-modality case-based CADx system is created by setting up a database of patients for a particular disease or illness. FIG. 1 shows an exemplary database of patients with breast cancer and the imaging scans that the patients have had. A database may contain image scans and non-image based information of the patients, including entries such as patient identifying information, demographic information (e.g., age, gender), patient clinical history (e.g., prior and current diseases, chief complaints), family history, vital statistics (blood pressure, weight, etc). The various image scan modalities may be, for example, film mammograms, ultrasounds, MRIs, digital mammograms, etc. For example, Patient 1 has had a film mammogram and an MRI scan, but no ultrasound. Patient 2 has had a film mammogram, ultrasound, and MRI, but no digital mammogram. Similar databases may be created for different cancers and illnesses and may include further image modalities such as CT scans, X-rays, PET scans, etc.

The system further analyzes a volume of interest ("VOI") across different modalities in order to find feature mapping from one modality to another. This information is used to populate a table which gives the ratios and mapping of feature values in one modality versus another. For example, one such method of mapping may be referred to as Factor Analysis, which may be used to map image-based features of one modality to image-based features of another modality. In order to map image-based features from one modality to another, a list of possible image-based features that may be extracted from an image is generated. These features are used to form a content matrix in which features correspond to different types of image modalities. The content matrix is then mapped based on available patient cases. Available patient cases may indicate non-image based features (e.g., age, gender, illness) and types of image modalities that are available.

Factor analysis is a statistical technique that may be used to reduce a set of variables to a set of smaller number of variables or factors. Factor analysis examines the pattern of inter-correlations between the variables, and determines whether there are subsets that correlate highly with each other but that show low correlations with other subsets or factors. Features that have low variance are eliminated and a concept value matrix is created in which mapping is generated between image features of one modality to image features of another modality. Thus, based on the results obtained from the factor analysis, an algorithm may be designed to generate case-based multimodality images given the extracted features from an image of an original modality.

Once there are a number of VOIs identified for a particular disease all the image-based features in multiple modalities are calculated. Factor Analysis is then used to infer the trends of features in the different modalities. Different features may even be related across modalities. For example, the density in one modality may be proportional to the texture in another modality. It should be noted, however, that it will be understood by those in the art that Factor Analysis is only one method of analyzing inter-correlations between variables and that any method of analysis may be used so long as it is able analyze features to infer trends of features in different modalities. An alternate method of analysis would be to use multivariate regression to map one set of features to another.

FIG. 2 shows a table of exemplary relative feature ratios across imaging modalities for a particular disease or illness. As described above, the feature table may be populated based on the results of the Factor Analysis, multivariate regression, or other method of analyzing features. Once this information is established, VOIs of one modality may be used to retrieve similar cases in other modalities. An image feature vector extracted from a VOI will allow initial retrievals of similar lesions in the same modality. The image feature vector is translated to image feature vectors for the other desired modalities.

In the exemplary table of FIG. 2, the CT modalilty features are indexed to the corresponding feature in different image modalities (e.g., ultrasound, MRI, X-ray) to create feature mapping. Feature mapping results in feature relationships between the same features or different features in different image modalities. For example, a spiculation feature of an ultrasound is 0.2 times that of a feature calculated from a CT scan, while a spiculation feature calculated from an MRI scan is 5.0 times that of a CT one. Thus, according to the exemplary values shown in FIG. 2, in order to convert spiculation from a CT scan to an ultrasound, the feature value calculated from the CT is multiplied by 0.2 while the same CT spiculation value is multiplied by 5 to convert to an MRI spiculation value. Similar conversions may be made for the remaining features (e.g., density, texture, average gray values, etc.). Thus, in the example of FIG. 2 the mapping is based on a simple ratio of feature values between different image modalities. It should be noted, however, that it will be understood by those skilled in the art that multiple features may be used to estimate the unknown feature value in a particular modality. Also, it could also happen in the above case that the speculations are unrelated in the modalities and completely different features are used to estimate speculation feature of a VOI in an ultrasound scan.

FIG. 3 shows an alternate method of converting features from different modalities by fitting a polynomial function to estimate the features in one modality from features in another modality. In the example of FIG. 3, an image-based feature may be graphed on a 2-dimensional graph with the x-axis representing feature calculated from one image modality and the y-axis representing the same feature from another image modality. The graph in FIG. 3 can be, for example, the spiculation in a CT scan as the x-axis and spiculation in an MRI scan can be the y-axis. The exemplary graph may then be fitted with a second-degree polynomial model. An exemplary second degree polynomial based on the curve values in FIG. 3 may be as follows: Spiculation-$_{MRI}$=0.4981+1.0231*Spiculation$_{CT}$−0.2942*[Spiculation$_{CT}$]$^2$. The equation of the polynomial model may then be used to map a feature of one image modality to the same feature in another image modality.

Thus, after the mapping of features of different image modalities is complete (e.g., as described above with reference to FIGS. 2-3), images or cases of different modalities corresponding to the case in question may be retrieved. This may be accomplished by initially extracting and mapping image-based features from the scan of the patient in question. These features are then compared to mapped features contained in a database of multimodality images. Once the image features have been mapped, an algorithm may be used to retrieve cases that include scans from other imaging modalities. The algorithm will compare a feature from the original image to corresponding features in the same type of images (e.g., CT feature to CT feature) and corresponding features from different modalities (e.g., CT feature to MRI feature). One such algorithm is disclosed in "Clinician Driven Example Based CADx" to Agnihotri et al., assigned U.S. Application 60/804,955. However, it will generally be understood by those of ordinary skill in the art that any number of algorithms may be used to retrieve cases with scans from other imaging modalities. For example, when a case to be diagnosed is accompanied only with a CT scan of the patient, the multimodality CADx system may retrieve similar CT scans, as well as MRIs, ultrasounds and other scans from the database.

Figure 4:
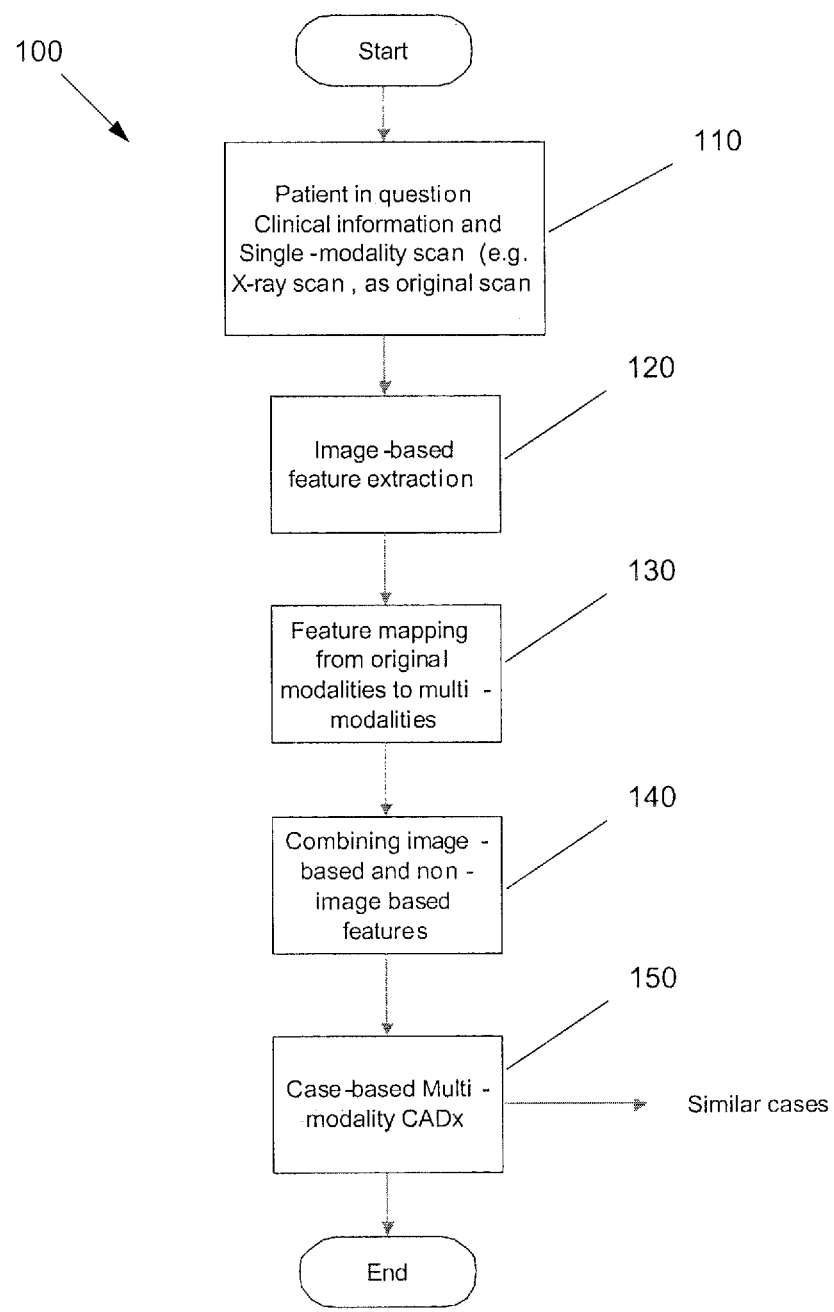
FIG. 4 shows an exemplary method for retrieving multi-modality images according to an exemplary embodiment of the present invention.

FIG. 4 shows an exemplary multimodality CADx system method 100, in which a single-modality scan of the patient to be diagnosed is taken in an original image modality in step 110. An image-based feature extraction is conducted on the original image in step 120. This extracted feature is then mapped from the original modality to multimodality images in step 130. For example, if the original patient scan is an X-ray scan, the features are extracted (e.g., density, texture, etc.) and mapped from the X-ray scan to other multimodality images (e.g., CT, MRI, ultrasounds, etc.). As described above, the relationship between features in different image modalities may be established, for example, by using ratios, as shown in FIG. 2, or by fitting a polynomial function to estimate features, as shown in FIG. 3. These relationships of the features may then be used in step 130 to retrieve other cases with images from the same or different modalities based on the image-based features of the original modality of the patient to be diagnosed.

The image-based features (image-based features from the original modalities and the mapped features) and the non-image based information of the patient in question may then be combined in step 140. That is, the features from the original modality may be combined with features calculated from images of a similar modality and features calculated from images from a different modality (e.g., features calculated from the CT scan of the patient in question to MRI features from retrieved images). For example, as described with respect to FIG. 1, other patient data may be associated with the various retrieved image, e.g., patient age, gender, chief complaints, current and prior diseases of the patient, family history, lifestyle, smoking history, etc. In step 140 these other non-image based features may be combined with the image based features. The combination of these features across all available image modalities and non-image clinical information of the patients may be used to create a case-based multi-modality CADx in step 150. Thus, by using a single modality image from step 110 (e.g., an X-ray), a physician in step 150 may be presented with additional X-rays having similar features, CT's, MRI's, Mammograms, etc. having similar features and the non-image patient data for these additional retrieved cases.

Figure 5:
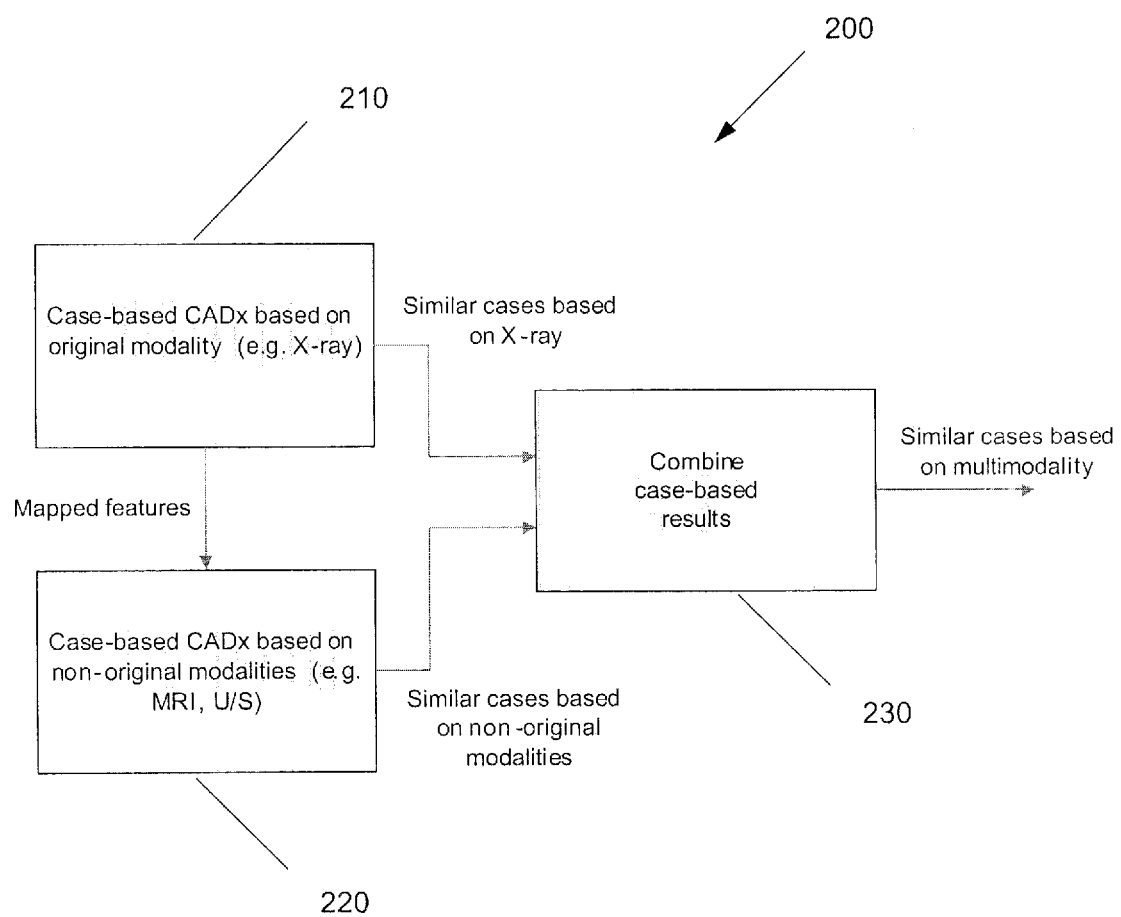
FIG. 5 shows a further exemplary method of retrieving multimodality images according to an exemplary embodiment of the present invention.

FIG. 5 shows another exemplary embodiment of a multimodality CADx system method 200. The method 200 may be sub-steps that are carried out in steps 130 and 140 of method 100. In method 200, a case-based CADx based on an original modality is created in step 210 in order to retrieve similar cases based on the original modality. For example, if the scan of the patient in question is an X-ray scan, the system 200 will retrieve similar, previously diagnosed X-ray scans based on features extracted from the X-ray scan of the patient in question and the corresponding features of the cases in the database. In step 220, images of non-original modalities are retrieved. As described above, based on previously analyzed data features from one modality are mapped to corresponding features of other modalities. A feature extracted from the original X-ray may be mapped to a feature in other modalities (e.g., a value for a feature in the original X-ray is converted to a corresponding value for a feature in another modality (CT, MRI, etc.). The corresponding features are then used to retrieve similar cases from the non-original modalities. For example, an original X-ray scan may be used to retrieve similar, previously diagnosed scans such as ultrasound, MRI, etc. The similar cases from the original modality 210 and the non-original modalities 220 are combined in step 230, for a final retrieval of similar cases based on the features in the original image. Step 230 may use any number of methods to combine the two results of 210 and 220. A distance calculation may be able to retrieve cases that have features closest to the scan presented, regardless of the image modality. Thus, if an X-ray scan is presented, a distance calculation may retrieve an MRI as having features closest to the scan presented.

Figure 6:
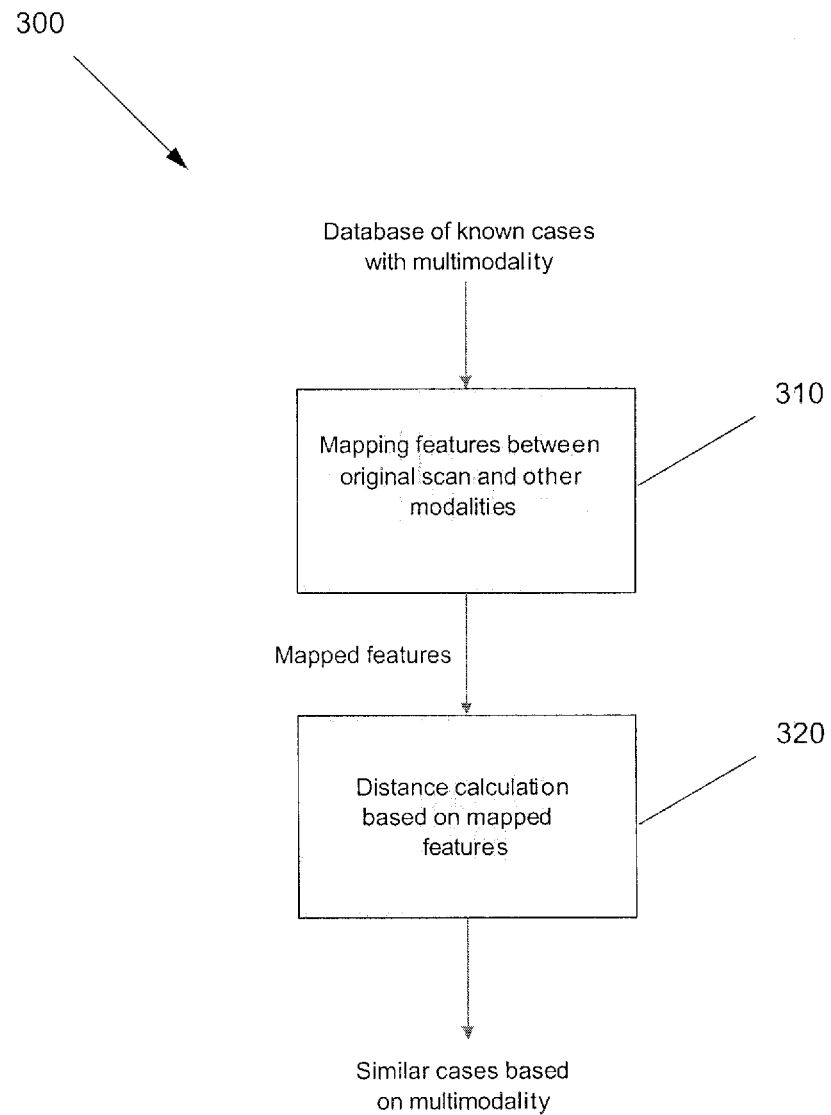
FIG. 6 shows an exemplary method for retrieving multi-modality images according to another embodiment of the present invention.

FIG. 6 shows a further embodiment of a multimodality CADx system method 300. The method 300 may also be sub-steps that are carried out in steps 130 and 140 of method 100. In steps 310, features for an original image are mapped to features in other modalities, in the same manner as described above for step 130 of FIG. 4. However, in step 320 these mapped features may be used to calculate distances to the multimodality images. A distance calculation may retrieve a patient's data whose combined images may have a closer distance than a single image of an original modality. For example, step 320 may retrieve a case in which a patient's combined X-ray and MRI scans have a closer distance than another X-ray alone. Those skilled in the art will understand that there may be numerous manners of finding distances based on different features that may be based on a variety of factors, e.g., types of images, related diagnoses, etc.

Through the use of the exemplary method and system, clinicians will be able to retrieve similar cases having different imaging modalities based on a single-modality image. Such a system allows clinicians to acquire knowledge by experience and referring to cases of a database of prior cases with known diagnosis. Thus, the ability to search and retrieve cases with images across various modalities will aid clinicians in their diagnoses and treatment planning.

It will be apparent to those skilled in the art that various modifications may be made in the present invention, without departing from the spirit or the scope of the invention. Thus, it is intended that the present invention cover modifications and variations of this invention provided they come within the scope of the appended claimed and their equivalents.

What is claimed is:

1. A method, comprising:
storing, on a non-transitory computer readable storage medium, a plurality of cases, each case including at least one image of one of a plurality of modalities and non-image information;
identifying, by a processor, at least one of the plurality of cases that contains images of a volume of interest across at least two different modalities;
extracting, by the processor, image-based features of the volume of interest from each image;
mapping, by the processor, a relationship between the features of the volume of interest across the different modalities to infer trends of features across different modalities;
storing the feature relationship on the non-transitory computer readable storage medium;
searching, by the processor, the non-transitory computer readable storage medium, wherein the searching comprises comparing a feature from an image of a current case to a corresponding feature in the at least one image of each of the plurality of stored cases based on the feature relationship, wherein the searching of images is across the multiple different modalities; and
retrieving, by the processor, at least one case within a predetermined threshold of similarity to the current case from the non-transitory computer readable storage medium.

2. The method of claim 1, wherein the non-image information includes one of patient identifying information, demographic information, patient clinical information, and family history.

3. The method of claim 1, wherein the mapping of the feature relationship is based on one of a factor analysis and a multivariate regression analysis.

4. The method of claim 1, further comprising:
simultaneously displaying the original image and the retrieved case.

5. The method of claim 1, further comprising:
calculating a distance between the extracted feature of the original image and a corresponding feature from the plurality of cases.

6. The method of claim 1, wherein the plurality of modalities are a film mammogram, an ultrasound, a CT scan, an MRI scan, a PET scan, an X-ray and a digital mammogram.

7. The method of claim 1, wherein the features of the volume of interest are a spiculation, a density feature, a texture feature, an average gray value, a shape feature, and a surface feature of a lesion.

8. A system, comprising:
a memory storing a plurality of cases, each case including at least one image of one of a plurality of modalities and non-image information; and
a processor identifying at least one of the plurality of cases that contains images of a volume of interest across at least two different modalities; extracting image-based features of the volume of interest from each image; mapping a relationship between the features of the volume of interest across the different modalities to infer trends of features across different modalities; searching the non-transitory computer readable storage medium, wherein the searching comprises comparing a feature from an image of a current case to a corresponding feature in the at least one image of each of the plurality of stored cases based on the feature relationship, wherein the searching of images is across the multiple different modalities; and retrieving at least one case within a predetermined threshold of similarity to the current case from the non-transitory computer readable storage medium.

9. The system of claim 8, wherein the processor maps the feature of the first modality to the feature of the second modality using one of factor analysis and multivariate regression analysis.

10. The system of claim 8, wherein the processor retrieves the at least one case based on calculating a distance between the extracted feature and a corresponding feature of the plurality of cases.

11. The system of claim 8, wherein the processor simultaneously displays the original image and the retrieved case.

12. The system of claim 8, wherein the plurality of modalities are a film mammogram, an ultrasound, a CT scan, an MRI scan, a PET scan, an X-ray and a digital mammogram.

13. The system of claim 8, wherein the features of the volume of interest are a spiculation, a density feature, a texture feature, an average gray value, a shape feature, and a surface feature of a lesion.

14. A system, comprising:
a means for storing a plurality of cases, each case including at least one image of one of a plurality of modalities and non-image information; and
a means for identifying at least one of the plurality of cases that contains images of a volume of interest across at least two different modalities; extracting image-based features of the volume of interest from each image; mapping a relationship between the features of the volume of interest across the different modalities to infer trends of features across different modalities; searching the non-transitory computer readable storage medium, wherein the searching comprises comparing a feature from an image of a current case to a corresponding feature in the at least one image of each of the plurality of stored cases based on the feature relationship, wherein the searching of images is across the multiple different modalities; and retrieving at least one case within a predetermined threshold of similarity to the current case from the non-transitory computer readable storage medium.

* * * * *